United States Patent [19]

Taylor et al.

[11] Patent Number: 5,087,256
[45] Date of Patent: Feb. 11, 1992

[54] THERMAL ATHERECTOMY DEVICE

[75] Inventors: James M. Taylor, Mountain View, Calif.; Eric L. Gay, Ann Arbor, Mich.; Mark J. Cowell, San Carlos, Calif.; David F. Wirt, Prescott, Wis.

[73] Assignees: Metcal Inc., Menlo Park, Calif.; Minnesota Mining and Manufacturing Company, St. Paul, Minn.

[21] Appl. No.: 593,790

[22] Filed: Oct. 5, 1990

Related U.S. Application Data

[63] Continuation-in-part of Ser. No. 464,399, Jan. 12, 1990, Pat. No. 5,047,025.

[51] Int. Cl.$^5$ .............................................. A61B 17/36
[52] U.S. Cl. ........................................ 606/28; 606/29; 606/31; 128/401
[58] Field of Search ............................. 128/399–402; 606/27–31

[56] References Cited

U.S. PATENT DOCUMENTS

| | | | |
|---|---|---|---|
| 3,903,891 | 9/1975 | Brayshaw | 606/27 |
| 4,627,436 | 12/1986 | Leckrone | 606/7 |
| 4,643,186 | 2/1987 | Rosen et al. | 606/33 |
| 4,654,024 | 3/1987 | Crittendon | 606/28 |
| 4,672,962 | 6/1987 | Hershenson | 606/28 |
| 4,685,458 | 8/1987 | Leckrone | 606/28 |
| 4,691,703 | 9/1987 | Auth | 606/31 |
| 4,708,136 | 11/1987 | Saito | 606/28 |
| 4,745,264 | 5/1988 | Carter | 219/553 |
| 4,747,405 | 5/1988 | Leckrone | 606/28 |
| 4,748,979 | 6/1988 | Hershenson | 606/28 |
| 4,785,815 | 11/1988 | Cohen | 606/7 |
| 4,790,311 | 12/1988 | Ruiz | 606/28 |
| 4,807,620 | 2/1989 | Strul | 606/28 |
| 4,839,501 | 6/1989 | Cowell . | |
| 4,899,741 | 2/1990 | Bentley | 606/27 |
| 4,978,346 | 12/1990 | Bentley | 606/28 |

FOREIGN PATENT DOCUMENTS 0352955 1/1990 European Pat. Off. .............. 606/28

OTHER PUBLICATIONS

"Electrical Thermal Angioplasty: Catheter Design Features, In Vitro Tissue Ablation Studies and In Vivo Experimental Findings"; David Y. Lu et al., The American Journal of Cardiology, Nov. 1, 1987, pp. 1117–1123.

Primary Examiner—Kyle L. Howell
Assistant Examiner—Robert L. Nasser, Jr.
Attorney, Agent, or Firm—Howard L. Rose

[57] ABSTRACT

A thermal atherectomy catheter has a tip of high magnetic permeability cylindrical stem with an enlarged head at one end and an enlarged collar at the other end, a coil of wire wrapped about the stem adjacent the head and removed from said collar, a sleeve of ferromagnetic material disposed about the coil and a second sleeve of non-magnetic outer sleeve extending between and of the diameter of the head and collar to define a space between the sleeves whereby the outer sleeve to collar are maintained at a lower temperature than the head.

21 Claims, 4 Drawing Sheets

THERMAL ATHERECTOMY DEVICE

RELATED APPLICATIONS

This application is a continuation-in-part of application Ser. No. 07/464,399 filed Jan. 12, 1990 now U.S. Pat. No. 5047025.

FIELD OF THE INVENTION

The present invention relates to catheters and the like and more particularly to steerable, heated catheters for removing atherosclerotic plaque from coronary as well as peripheral arteries.

BACKGROUND OF THE INVENTION

Atherosclerotic plaque is a relatively common occurrence in these times of rich foods and long life. The plaque produces a stenosis reducing the diameter of the lumen of the artery and restricting blood flow to the region beyond the stenosis. In some instances a balloon catheter may be employed to increase the diameter of the lumen particularly where complete blockage of the artery has not occurred. The balloon increases the diameter of the vessel by stretching the wall beyond the limit of elastic recovery but does not compress plaque that has hardened. In those instances where a balloon catheter cannot be used or cannot be used initially, catheters may be used t bore through the plaque and increase the diameter of the lumen through the stenosis so that if necessary a balloon catheter may be employed.

The use of steerable catheters to remove atherosclerotic plaque both from coronary as well as peripheral arteries is in increasing use today. In the art today, there are heated catheters, cutting blade catheters and various types of laser catheters all of which may be quite dangerous in use since, if aimed incorrectly or overheated, they can damage the wall of an artery producing serious, if not fatal, injury or cause particles to enter the blood stream.

Various approaches to reducing these hazards have been suggested. Very thin guide wires may be employed to facilitate guiding the catheter to the proper location. Although probably not used in practice, some patents disclose feeding a laser through the arteries to remove plaque. To better control various factors such as size of the instrument, aim of the beam and the energy supplied by the laser, optical fibers are now employed to conduct laser energy to the site of the stenosis.

Various of these techniques are being employed today but dangers of overheating and misdirection are still prevalent although the use of guide wires has materially reduced the danger of mechanical puncture of the wall of an artery. Further, there is still the danger that solid debris from the plaque or liquified plaque may enter the blood stream and produce serious blockage, particularly in small coronary arteries.

The use of a heated catheter requires a delicate balance of various factors. It is desirable to concentrate the heat in an axially forward direction at the distal face of the heater of the catheter while maintaining the sides of the catheter at a relatively low temperature. The distal face of the catheter must be able to rapidly reach a temperature that produces vaporization of the plaque. As to the range of allowable temperatures of the sidewall of the catheter, the upper end of the range must be below a temperature at which the catheter will stick to the wall of the artery, or approximately 120° C. Such temperature, however, should be high enough to damage without charring the inner surface cells of the wall so that the rate of future adherence of plaque to the wall will be greatly reduced.

Such control of sidewall temperature of a heated catheter can be achieved by maximizing forward heat flow while carefully controlling flow of heat from the distal face of the heater towards its proximal end and radially from the core of the heater to the sidewall whereby the length of the sidewall behind the head that is at temperatures that can produce sticking is sufficiently short as to not allow sticking during use.

BRIEF DESCRIPTION OF THE PRESENT INVENTION

In accordance with the present invention there is provided a catheter with a heater at its distal end for use in removing atherosclerotic plaque in coronary and peripheral arteries, which catheter has a temperature self regulating heater built into its distal end. Preferably the catheter operates in conjunction with a guide wire so as to be guided along an artery to the location of a stenosis. A fine guide wire can be more readily manipulated than a catheter and, as such, greatly reduces the danger of entering a wrong artery or puncturing the wall of an artery. The catheter ca be easily slid along the guide wire to the desired location.

In the present invention the use of the guide wire in conjunction with a temperature self regulating heater removes the most common dangers in the use of such instruments. The use of the guide wire is not essential but when the catheter is constructed such as to be usable with a wire, the margin of safety is greatly increased.

The present invention employs a temperature self regulating heater, with regulation of temperature being accomplished by employing a material having a high magnetic permeability such as a ferromagnetic, ferrimagnetic or the like material having a Curie temperature at the maximum temperature of heater operation. As pointed out in U.S. Pat. No. 4,914,267 a ferromagnetic conductor connected in series in a circuit having a high frequency, constant current supply or subject to a varying magnetic field at such high frequency regulates temperature up to and about the effective Curie temperature of the ferromagnetic material. The effective Curie temperature is that at which the material becomes sufficiently close to paramagnetic for purposes of operation of the heater in the present environment. Such temperature may however be a few or as much as 100 degrees less than absolute Curie temperature where the material becomes truly paramagnetic.

The high mu material increases in temperature until the effective Curie temperature is approached. As this occurs the resistance of the heater decreases and, since current is constant (K), the power dissipation is controlled by the equation: $P = KR$. The reduction in resistance causes a reduction of power dissipation. The heater stabilizes at an equilibrium temperature which is maintained until the load on the heater changes and the heating cycle is repeated until equilibrium is again established.

In a magnetic flux coupled heater the high mu material is subject to a high concentration of magnetic flux causing the material to heat. Upon approaching Curie temperature, the material becomes generally paramagnetic or the permeability is so reduced that the flux coupling is greatly reduced and the heater cools until an equilibrium condition is again established.

The temperature of the device at the stenosis must be such as to ablate the plaque by vaporization, thus preventing pieces of the plaque or melted plaque from entering the blood stream. Also the design of the structure must be such that at such a temperature only a desired degree of damage is done to the walls of the artery. It is desirable to damage, without charring, the cells of the inner surface of the artery so as to reduce the rate of buildup of plaque in the future.

The Curie temperature of the high mu material is the maximum temperature of the device which, in practice, is not often achieved but is approached when the stenosis is engaged and blood is essentially excluded from the region of contact. The operating temperature range of the various Curie temperature materials employed in conjunction with the structure described below is a function of the environment in which employed. It is essential that the temperature of the distal face contacting the plaque be above 300° C. It has been found that at a heater Curie temperature of 400° C. the catheter will tend to stick to the walls of the vessels. Thus materials having Curie temperatures of 450° C. to approximately 620° C. are desired and have been found satisfactory, the latter permitting a more rapid procedure, decreasing the margin of thermal damage to the walls of the arteries by decreasing the transit time through the stenosis. The Curie temperature selected provides the utility and safety of a rapid procedure with only a quite short length of sidewall at temperatures that can produce sticking, that is, temperatures of 120° C. or more.

The present invention contemplates thermal atherectom catheters preferably movable along a guide wire for purposes of removing plaque from coronary and peripheral arteries. The size of the catheter described herein is employable in distal peripheral and the coronary arteries. In most instances the heater comprises a hollow, cylindrical body of, for instance, a ferromagnetic material having a flared head at one end, the distal end, of the cylinder. An integral collar is located adjacent the other, proximate, end of the hollow cylindrical heater and insulated wire is wound helically in several layers about the cylindrical body between the head and the collar. The wire (coil) is potted in a thermally conductive electrically insulative material and a thermally conductive ferromagnetic metal tube or sleeve of lesser diameter than the head surrounds the potted coil. A further metal tube or sleeve of the diameter of the head extends from the head to the collar providing an insulating space between the two sleeves. This space may be filled, for instance, by microshells fused to one another to provide a complete filler which is 95% to 98% air.

The inner metal sleeve is a 400 series stainless steel which is ferromagnetic while the outer sleeve is a 300 series stainless steel which is non-magnetic. The preferred materials are stainless 430 and 316, respectively. The coil is not as long as the space between head and collar and is disposed immediately adjacent the head s that the magnetic flux produced by the coil is coupled directly to the head as well as the cylindrical body and inner sleeve while having little coupling to the collar. In consequence of this arrangement, that is, the coil remote from the collar with magnetic flux and heat coupled directly to the head as well as the cylindrical body and inner sleeve, the insulating space between the inner and outer sleeve and potting with a heat conductive material, the heat is concentrated in the head. Also the ferromagnetic sleeve of 430 stainless together with the non-ferromagnetic outer sleeve concentrates the flux radially inward of the catheter thus increasing efficiency and reducing radiation of magnetic flux into surrounding tissue. The only region of the device that both develops high temperature and radially contacts the wall of the artery is the very short edge of the head and a short length of the sidewall and thus in conjunction with appropriate use of the device, thermal damage is held to desired levels. The maximum diameter of the device varies with intended use and typically with peripheral arteries may vary from 0.04 to 0.16 inch.

The helically wound wire is brought out through a slot in the collar and is connected to a coaxial cable. A tube which carries a guide wire to the interior of the hollow cylindrical heater is encased, along with the coaxial cable, in an outer casing which, depending upon use, may or may not be enclosed within a spiral spring. An anchor wire is attached to the heater to prevent its detachment from the remainder of the catheter. The wire may be electrically conductive or coated with an electrically conductive material to prevent build-up of static electricity on this heater.

In use, entry is made into an artery that leads to the artery to be treated. A guide wire is inserted through the entry into the artery and while being observed by fluoroscopy is guided through the stenosis. Once the guide wire is satisfactorily located distal to the stenosis, the catheter is advanced over the guide wire until it reaches the stenosis. The coaxial cable is attached to an appropriate power supply, the power supply is turned on and the heater energized by magnetic flux produced by the coil when power is applied, typically by means of a foot pedal switch.

The heater to be described herein is operated preferably at about 13.56 MHz and has an effective Curie temperature preferably in a range of 450° C. to 620° C. and perhaps as high as 700° C. The frequency of operation may vary depending upon size of the device, materials employed and the like and may vary from 10 MHz to 2 GHz. Specifically, the wattage of the power supply must be such as to cause the heater temperature to increase rapidly at lower temperatures and to have such high power operation as to rapidly re-establish desired temperature in the presence of a sudden increase in thermal load. Thus, the heater provides therapeutic ablation by vaporization with operating cycles as short as one second. Since the environment in which the various heaters will be employed varies with their use and thus a fixed figure is not possible, it appears that 18–42 watts at 13.56 MHz is sufficient at the power supply.

It is thus a primary object of the present invention to provide a small, temperature self regulating heated catheter for use in removing plaque from arteries of humans and animals, which catheter may be employed with a guide wire and which minimizes danger to the walls of the arteries.

DETAILED DESCRIPTION OF THE PRESENT INVENTION

Figure 2:
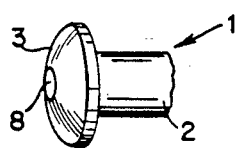
FIG. 2 illustrates the core and head end of the heater of the catheter.
Figure 3:
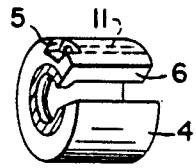
FIG. 3 illustrates the collar which is fabricated as an integral part of the core and head but shown separately for purposes of clarity.
Figure 1:
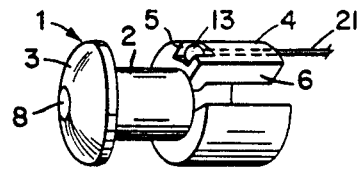
FIG. 1 illustrates the head end, core and collar of the heater as a unitary structure.

Referring now specifically to FIGS. 1-3 of the accompanying drawings, there is illustrated a heater 1 of the catheter fabricated from material of high magnetic permeability, which term includes ferromagnetic, ferrimagnetic and like material. The heater 1 includes a hollow cylindrical body 2 terminating at its distal end in an enlarged round, dome-shaped head 3 and at its proximate end in a collar 4, both coaxial with the cylindrical body 2. Center bore 8 of the heater 1 should accommodate a guide wire of not more than, 0.016 inch diameter.

Figure 4:
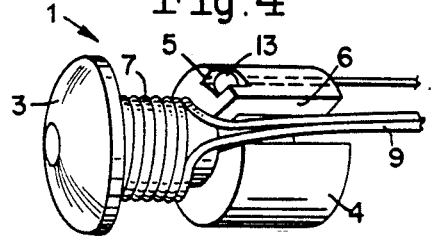
FIG. 4 illustrates the assembled heater with the potted heater winding wound about the core

The collar 4, a unitary structure with the head and body 2, and the head and body 2 are illustrated separately in FIGS. 2 and 3, respectively, for purposes of clarity only. The collar 4 is cylindrical and has a slot 6 extending parallel to the axis of the collar for purposes to be described. The heater 1 may be secured, by welding, for instance, to an anchor wire, to prevent loss of the heater 1. Preferably, however, the collar has a rectangular recess 5 in its distal edge as viewed in FIGS. 1 and 2 communicating with a hole 11 extending axially through the remaining region of the collar so that an anchor wire 21 with a bulbous end 13 may be threaded through the hole with the bulbous end 13 seated in the recess 5. The anchor wire may have a thin coating of copper or other electrically conductive material to provide a conductive return to drain off static electricity. A wire of appropriate diameter (0.15 mm or 34-40 AWG) is wound about the body 2 to form a coil 7 with its ends (wires) 9 brought out through the slot 6 in the collar; FIG. 4.

In one embodiment, the heater 1, body 2, head 3 and collar 4 are fabricated from a Type 430 stainless supplied by Carpenter Steel Division of Cartech. The wire is 0.27% nickel clad high temperature copper wire having a ceramic coating for electrical insulation.

Figure 5:
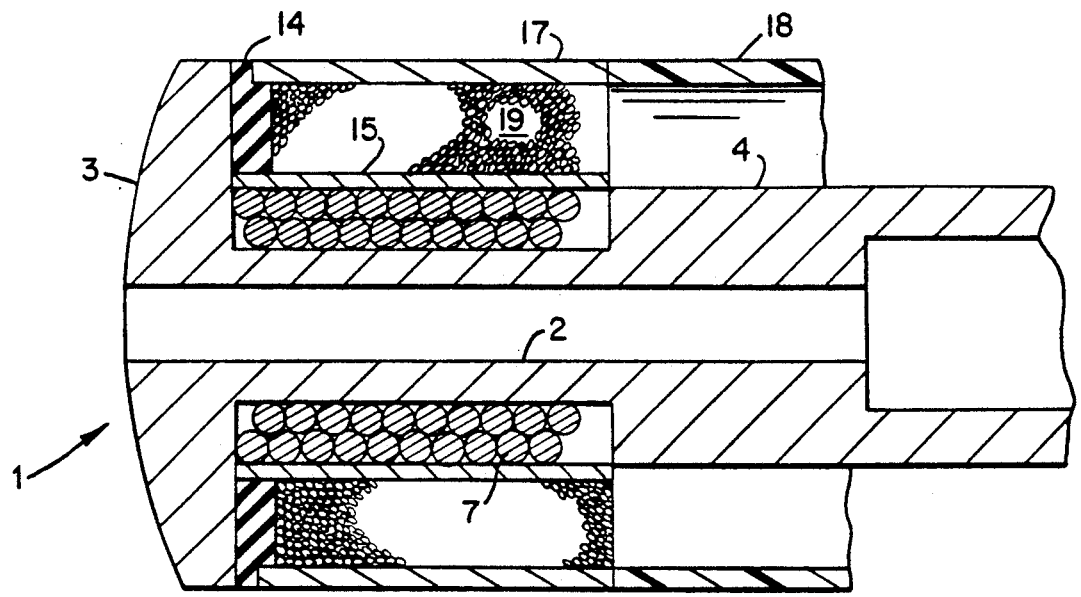
FIG. 5 illustrates in cross section the completed core, collar and potted winding.

Referring now specifically to FIG. 5, the coil 7 is wound to be abutting the head 3 and spaced from the collar 4 to cause flux to couple to and provide some direct heating in the head. Conversely the coil 7 is maintained a distance from the collar 4 to reduce coupling to and thus heating in the collar.

The coil 7 is potted in a heat conductive material, for instance 50-50 mixture TGC 120 borosilica glass and Type 1500 crossover paste or other suitable material. The potted coil is surrounded by a sleeve 15 of stainless steel of the 400 series (preferably 430SS). The sleeve 15 has an internal diameter approximately equal to the diameter of the collar 4 and concentrates the flux in the region defined by the sleeve increasing efficiency, reducing flux coupling to the collar and also reducing radiation external to the catheter.

Figure 6:
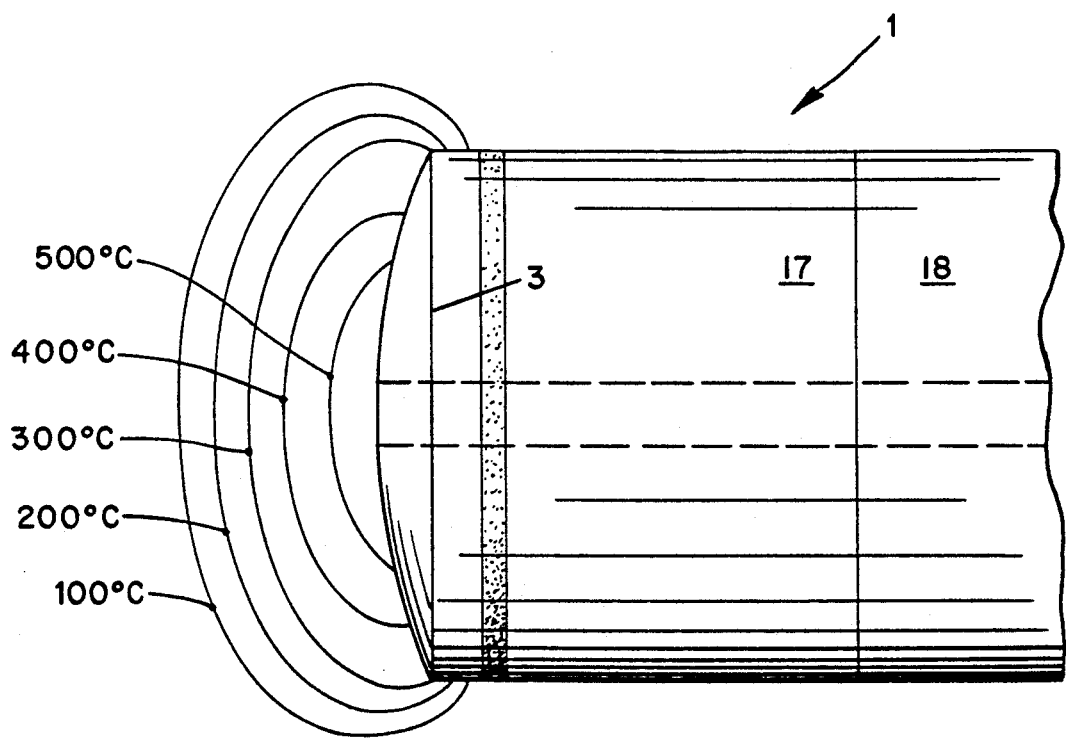
FIG. 6 illustrates an idealized temperature profile about the head of the heater of the catheter in a homogeneous medium.

The combination of the placement of the coil 7, the use of heat conductive potting compound and sleeve 15 which is also heated by the flux developed by the coil, forms an axially thermally conductive structure that insures a concentration of heat in the head 3. An idealized heat pattern adjacent the head is illustrated in FIG. 6 of the accompanying drawings.

A sleeve 17 of series 300 stainless steel (preferably 316SS), extends from the head 3 to a region radially aligned with the proximate end of the collar 7 remote from the head, but spaced radially outward from the collar 4. A thermally insulating body 14 of adhesive (S prime-mod from Zyp Coatings, Inc.) is disposed between sleeve 17 and head 3 to bind the sleeve to the head while providing some insulation of sleeve 17 from the adjacent head temperature. The sleeves 15 and 17 define a space 19 to maximize radial thermal resistance. The space 19 may be filled with microshells 21 that are fused together to provide a solid mass that excludes ambient air but which is 95% to 98% air. The microshells are available from the 3M Co. and others. Thus the only significant heating of the sleeve 17 is by conduction from the head 3 via body 14, which maintains the sleeve temperature below charring temperature and below sticking temperatures except over a short enough length immediately adjacent the head that sticking occur.

Figure 7:
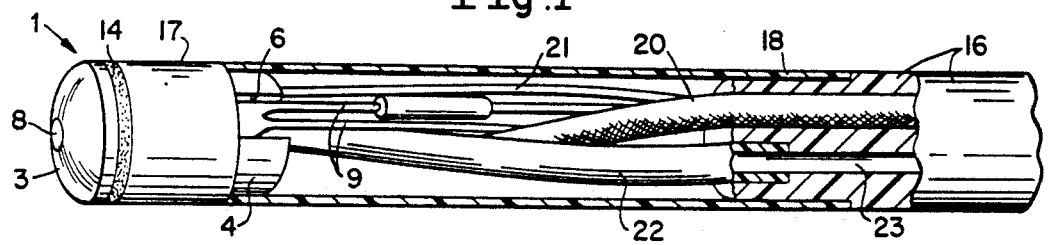
FIG. 7 illustrates the initial connections of the assembly of FIG. 5 in a cable connected to the external components of the device.
Figure 8:
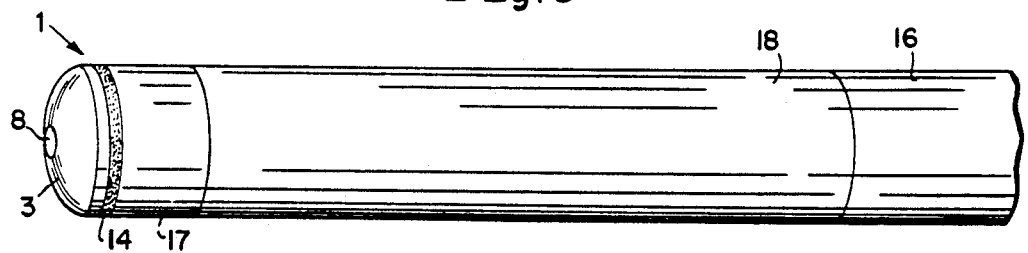
FIG. 8 illustrates the completed connection of the heater assembly to the cable.
Figure 9:
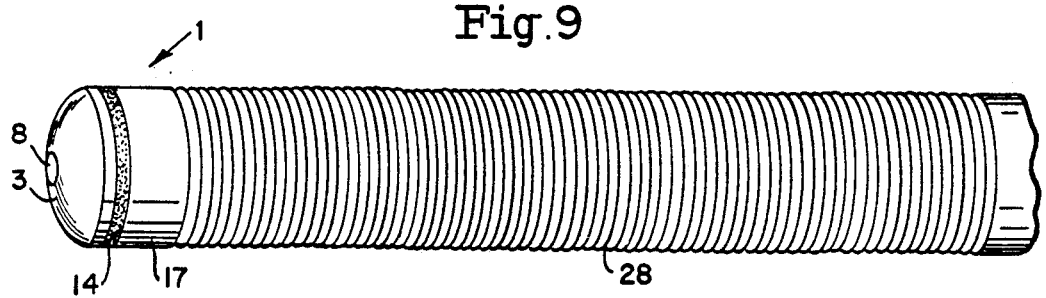
FIG. 9 illustrates the application of a spiral external spring to the assembly of FIG. 8.

Referring now specifically to FIG. 7 of the accompanying drawings, one of the coil leads 9 is connected to the center conductor of a coaxial cable 20 that serves as a transmission line, while the other wire 9 is connected to the braid of the cable 20. A hollow tube 22 has one end aligned with axial passage 8 through the heater 1. The lumenal extension of this tube extends to the end of the cable structures as discussed relative to FIG. 10 and is adapted to receive a guide wire which may pass through the tube 22 and into and through the passage 8 in the heater 1. Dye may also be injected into the artery through the tube 22 and passage 8. The coaxial cable 20 and a lumen extending from tube 22 extend through a flexible hollow tube (extrusion) 16, which may be polyurethane, to the proximal end of the instrument. The anchor wire 21 used to prevent loss of the distal end of the catheter and which may be used as a ground wire is secured to the collar 4 and extends through the extrusion 16 to a three-port-Y=26, see FIG. 10, where it is anchored. The region between the proximal end of the core 2 and the extrusion 16 is potted, a typical potting material being a Type A medical, adhesive silicon. A PTFE sleeve 18 (FIG. 8) extends from the proximal end of the heater (collar) to the distal shoulder of the extrusion 16 to complete construction thereof. If desired in a particular application, an elongated spiral spring 28 (FIG. 9) may be disposed about the catheter from adjacent the collar 4 to a region of the extrusion 16.

At the end of the extrusion 16 remote from the catheter heater 1, two members are brought out, a lumen 23 in extrusion 16 which is aligned with the tube 22 and the coaxial cable 20.

Figure 10:
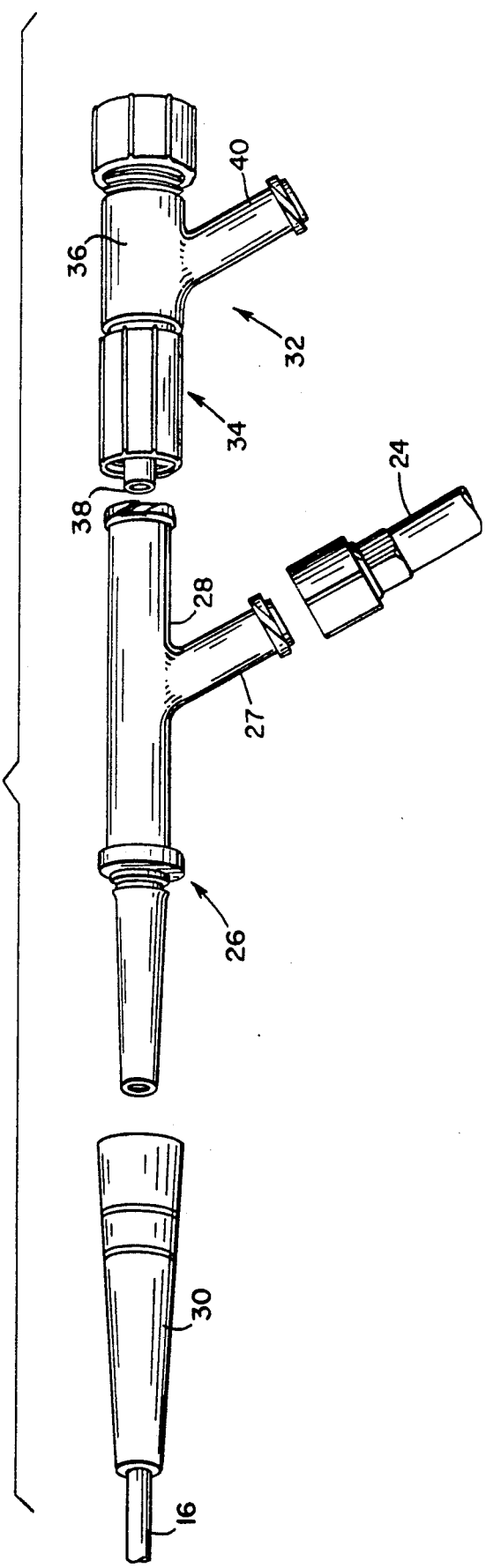
FIG. 10 illustrates the members involved in the connections of the cable to the external components of the system employing the catheter.

Referring now to FIG. 10, there is illustrated an exploded view of the connections to the extrusion 16 at the end remote from the heater 1. The extrusion 16 passes through a sleeve 30 of flexible material employed to protect the end of the extrusion. Secured inside of the sleeve is the three-port termination 26 internally of which the extrusion 16 terminates. The coaxial cable 20 is brought out through port 27 to a coaxial connector 24. Attached to a second port of the three-port termination 26 is a Tuohy-Borst Adapter 32 or the like inserted in the end of port 28, the adapter 32 having a swivel 34 which permits a main body member 36 of the adapter to be rotated about the axis of the port 28. The main body member 36 has a central bore 38 communicating through the swivel with the lumen 23 of the catheter; the central bore being adapted to sealably receive the guide wire while allowing movement of the guide wire. The main body member 36 has a side arm 40 that communicates by the central bore 38 and is adapted to receive fluid which may contain a contrast media for injection into the catheter and through the hole 8 in the heater and thus into the artery.

In use, a guide wire, if one is employed, is inserted into an artery via an introducer or a guiding catheter and guided to the location of and through the stenosis. The heater catheter is then threaded onto the wire at its proximal end external to the patient's body and slid through the introducer or guiding catheter and along the wire until it reaches the stenosis. The heater is brought into contact with the stenosis and is then activated to ablate the plaque to either create a passage through the plaque or to widen an existing passage whereby in either event to increase blood flow through the affected region. The procedure may, under appropriate circumstances, substantially clear the blockage or produce a passage large enough to permit adjunctive balloon angioplasty.

As previously indicated there are two main concerns relating to catheters employed primarily to remove atherosclerotic plaque from human arteries. The first concern relates to minimizing introduction of liquified plaque and/or charred pieces of vessel wall into the blood stream. The present device addresses these purposes by employing materials having high magnetic permeability that regulate at temperatures that ablate by vaporization the plaque so that it is absorbed into the blood in gaseous and fine particle form thus minimizing the dangers incident to its removal. Acceptable vaporization temperatures lie in the range of approximately 350° C. to 500° C. and specifically above 300° C. below which temperature the catheter may stick to the walls of the artery and ablation rates are too low.

The second concern with the use of thermal catheters relates to damage to the walls of the artery due to excessive heat. By employing a structure where the heat is generated at the head 3 of the heater 1, and the core of the heater is surrounded with a coil, and the coil is surrounded with materials that are good heat conductors and a space is provided between the coil and outer sleeve, sidewall of the heater, the sides of the heater 1 are maintained except for a very short length at a temperature below that of the core and the head 3; the latter being a direct extension of the core. The heat employed to vaporize the plaque is primarily dissipated at the distal face 3 and is thus applied primarily to the plaque as opposed to the arterial walls. The present invention provides rapid reduction of temperature along sleeve 17 so as to minimize the length of the region of temperatures that can produce sticking. This region can be further reduced by placing a further sleeve in the heater to provide a region between this additional sleeve and sleeve 17 into which cooling fluid may be introduced. Cooling fluid could be circulated through a further port in the connector 26 containing input and output tubes connected to a fluid temperature control apparatus.

Figure 11:
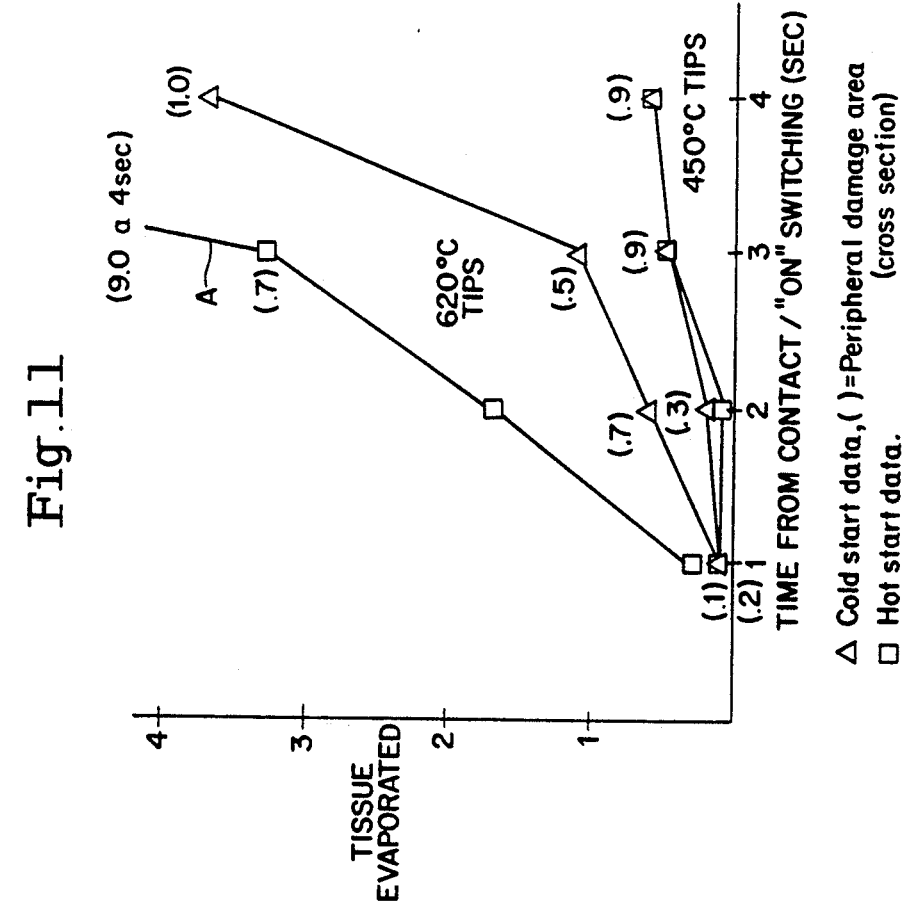
FIG. 11 comprises a series of graphs illustrating tissue ablated versus time for catheters of two different Curie temperatures.

Referring specifically to FIG. 11 of the accompanying drawings, there is illustrated a graph of the axial cross-sectional area of tissue ablation by the present catheter as a function of time, for heaters having Curie temperatures of 450° C. and 620° C. It is readily apparent that the higher Curie temperature catheter vaporizes tissue at a far greater rate than the lower temperature catheter. The peripheral (wall) damage margin (cross-sectional area) is given in parentheses at each of the graph points. Damage for Graph A after 3 seconds is 0.7 mm$^2$, an acceptable margin, roughly equivalent to that caused by a scalpel blade at the same depth.

It is apparent that the greater the power available to the heater, the faster it will rise to temperature and hold temperature in the face of changing, specifically, increasing load. The load varies greatly with the rate at which it is attempted to move the catheter through a blockage so that the more power that is available the more uniform the temperature will remain and the more quickly can the catheter be moved. As in any invasive procedure, it is most desirable to go in and get out as quickly as is commensurate with safe procedures and adequate reduction of stenosis.

Figure 12:
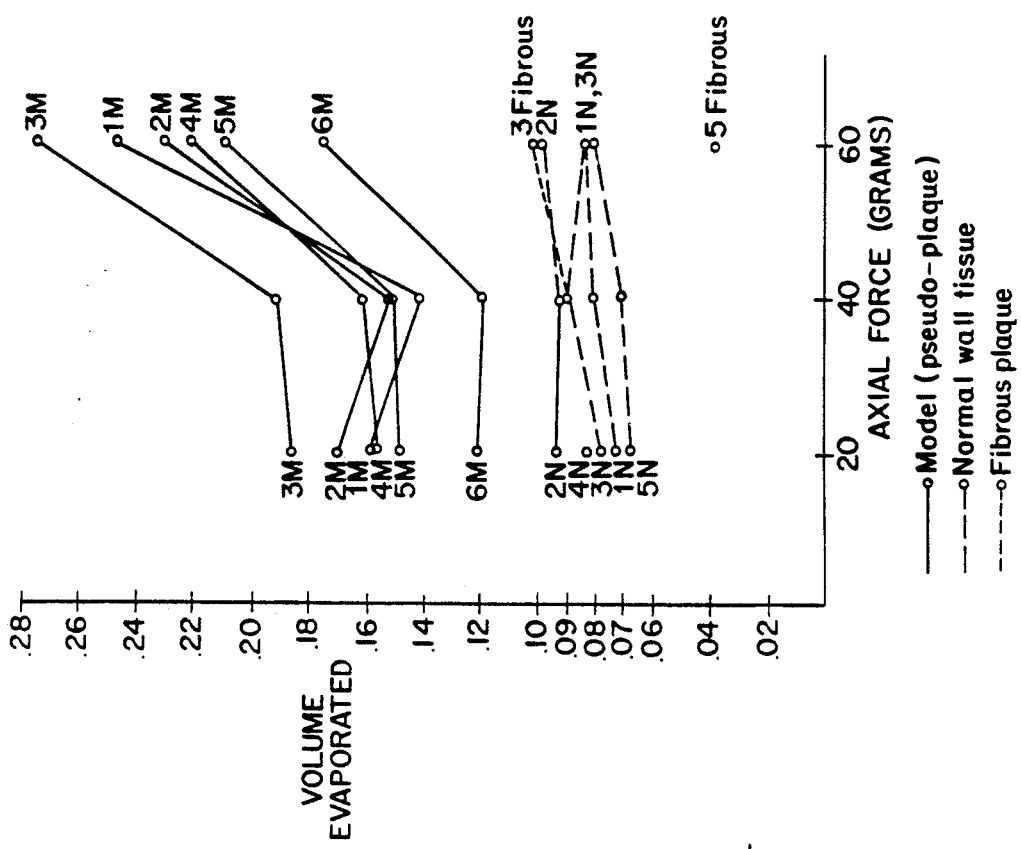
FIG. 12 is a series of graphs illustrating ablation rate per unit energy as a function of axial force for a series of prototype catheters having various heater and overall diameters, the values of the No. 3 device approximating those of the device described in this application.

In FIG. 12 of the accompanying drawings the ablated volume is plotted as a function of axial force in grams for three different types of "blockage" materials. The numerical designations are: 1 and 2 discontinued models, 3 is an 80 thousandth inch outside diameter head, 4 is a 60 thousandth outside diameter head, 5 is a 70 thousandth outside diameter head and 6 failed. The model (pseudo-plaque) is polyurethane gel of 90% water.

The term "constant current" as used herein refers to a current, I, where:

$$\frac{\Delta |I|}{I} < -1/2 \frac{\Delta |R|}{R}$$

The degree of self regulation is a function of the differences in degree of change of the two sides of the equation. If $\Delta |I|$ is equal to zero, good regulation is achieved as set forth in U.S. Pat. No. 4,914,267. As the value of the left side of the equation approaches that of the right side, the degree of self regulation decreases. The power supply used may be any one of the supplies described in U.S. Pat. Nos. 4,626,767, 4,752,864, 4,795,886 or 4,769,519 or other controlled current power supplies available on the market that can produce frequencies in the megacycle range. The first two supplies mentioned above by patent number operate at 13.56 MHz, preferably.

Many variations and modifications of the above-described embodiments are within the ordinary skill of the skilled artisan in this art, without departing from the scope of the invention. Accordingly, those modifications and embodiments are intended to fall within the scope of the invention as defined by the following claims.

We claim:

1. A thermal atherectomy catheter for use in blood vessels and the like comprising
   a tip of high magnetic permeability including a cylindrical body terminating at one end in an enlarged head and at its other end in an enlarged collar,
   a coil of wire adapted to be connected to a source of current wound about said cylindrical body essentially abutting said head and removed from said collar.

2. A thermal atherectomy catheter according to claim 1 further comprising
   a high magnetic permeability cylindrical sleeve disposed in close proximity about said coil and of less diameter than said head,
   said coil being enclosed within a heat conductive potting compound within said sleeve.

3. A thermal atherectomy catheter according to claim 2 further comprising
   a non-magnetic sleeve of a diameter of the head and extending between said head and said collar to define an airspace between said sleeves.

4. A thermal atherectomy catheter according to claim 3 further comprising
   a poor heat conductor filling the space between said sleeves.

5. A thermal atherectomy catheter according to claim 3 or 4 further providing
   a poor heat conducting material for securing said non-magnetic sleeve to said head.

6. A thermal atherectomy catheter according to claim 1 wherein
   said tip has an axial passage therethrough to receive a guide wire.

7. A thermal atherectomy catheter according to claim 1 wherein
   said high permeability magnetic material has a Curie temperature above 400° C.

8. A thermal atherectomy catheter according to claim 7 wherein said Curie temperature lies in a range of 450° C. to 700° C.

9. A thermal atherectomy catheter according to claim 1 further comprising
   a non-magnetic sleeve of about the diameter of said head and collar and extending between said head and collar, and
   means for maintaining all but a short length of said sleeve adjacent said head below a temperature at which said sleeve sticks to wall of the blood vessel.

10. A thermal atherectomy catheter according to claim 1 further comprising
    means for preventing static voltage build-up on said catheter.

11. A thermal atherectomy catheter according to claim 10 wherein
    said means comprises an anchor wire for said tip.

12. A thermal atherectomy catheter according to claim 11 wherein
    said anchor wire is secured to said collar.

13. A thermal atherectomy device comprising
    a cylindrical body of high magnetic permeability material terminating at one end in an enlarged head,
    said high magnetic permeability material having Curie temperature sufficient to vaporize plaque in arteries,
    a sleeve of non-magnetic material extending from said head coaxially of and radially spaced from said cylindrical body,
    means for raising the temperature of said head to about its effective Curie temperature, and
    means for maintaining the temperature of a substantial length of said sleeve below a temperature at which the device sticks to the walls of the arteries.

14. A thermal atherectomy device according to claim 13 wherein
    said means for raising temperature is a coil of wire wound about said cylinder adjacent said head and,
    means for connecting said coil to a source of alternating current.

15. A thermal atherectomy device according to claim 13 wherein said means for maintaining comprises
    a sleeve of high magnetic permeability disposed about said coil and aligned with and of lesser diameter than s id first mentioned sleeve.

16. A thermal atherectomy device according to claim 15 said means for maintaining further comprising
    means for effectively maintaining an essentially low heat conductive medium in a region between said sleeves.

17. A thermal atherectomy device according to claim 15 or 16 wherein said means for
    maintaining further comprises a low heat conductive sealant disposed between said first mentioned sleeve and said head.

18. A thermal atherectomy device according to claim 13 wherein said cylinder has a passage therethrough coaxial with said head and said cylinder.

19. A thermal atherectomy device according to claim 18 further comprising a hollow tube communicating with said passage, and
    wherein said means for connecting includes a coaxial cable connected to said coil and connectable to a source of constant current.

20. A thermal atherectomy device according to claim 19 adapted for thermal angioplasty wherein the transmission line is constructed and arranged to pass through a blood vessel so that the occlusive effect of plaque residing within the vessel may be reduced.

21. In an interventional therapeutic apparatus for remote delivery of heat to body tissue, the combination which comprises:
    a. an oscillator for providing an r.f. output signal within the range of 10 MHz to 2 GHz;
    b. a transmission line having a proximal end connected to the oscillator for receiving the output signal and a distal end, the transmission line being constructed and arranged to pass through the interior of a body cavity;
    c. an inductive load disposed at the distal end of the transmission line, the inductive load comprising a magnetic material and operating to convert the r.f. signal transmitted through the transmission line into heat the conversion being optimized at a predetermined frequency; the frequency of the output signal from the oscillator being set at substantially the predetermined frequency, whereby the inductive load is heated to a temperature sufficient for therapeutic effects, and
    said inductive load including a ferromagnetic material and a coil of wire wound about said ferromagnetic material to heat said ferromagnetic material upon connection of said coil across a source of laternating current.

* * * * *